United States Patent
Blunsden et al.

(10) Patent No.: US 9,878,113 B2
(45) Date of Patent: Jan. 30, 2018

(54) PRESSURE CONTROL IN RESPIRATORY TREATMENT APPARATUS

(75) Inventors: Christopher Kingsley Blunsden, Newport Beach (AU); Ronald James Huby, North Epping (AU); Graham Stephen Cutcliffe, Caringbah (AU); Jack Wei Cheng, Marrickville (AU); Zhuo Ran Tang, Maroubra (AU)

(73) Assignee: ResMed Limited (AU)

( * ) Notice: Subject to any disclaimer, the term of this patent is extended or adjusted under 35 U.S.C. 154(b) by 1938 days.

(21) Appl. No.: 12/996,803

(22) PCT Filed: Jun. 2, 2009

(86) PCT No.: PCT/AU2009/000689
§ 371 (c)(1),
(2), (4) Date: Mar. 11, 2011

(87) PCT Pub. No.: WO2009/149490
PCT Pub. Date: Dec. 17, 2009

(65) Prior Publication Data
US 2011/0174308 A1    Jul. 21, 2011

Related U.S. Application Data

(60) Provisional application No. 61/061,256, filed on Jun. 13, 2008, provisional application No. 61/097,591, filed on Sep. 17, 2008.

(51) Int. Cl.
*A61M 16/00*    (2006.01)

(52) U.S. Cl.
CPC ........ *A61M 16/00* (2013.01); *A61M 16/0069* (2014.02); *A61M 2016/0021* (2013.01); *A61M 2205/18* (2013.01)

(58) Field of Classification Search
CPC .......... A61M 2016/0039; A61M 16/00; A61M 2016/0021; A61M 16/0825;
(Continued)

(56) References Cited

U.S. PATENT DOCUMENTS 4,326,513 A * 4/1982 Schulz et al. ............ 128/203.14
6,085,747 A    7/2000 Axe et al.
(Continued)

FOREIGN PATENT DOCUMENTS

| EP | 0 661 071 A1 | 7/1995 |
| EP | 0722747 A2 | 7/1996 |
| WO | 2004078246 A1 | 9/2004 |
| WO | 2008025080 A1 | 3/2008 |

OTHER PUBLICATIONS

Extended European Search Report for Application No. EP09761155 dated Dec. 22, 2015.
Partial Supplementary European Search Report for Application No. 09761155.2 dated Aug. 17, 2015.

*Primary Examiner* — Lynne Anderson
(74) *Attorney, Agent, or Firm* — Botos Churchill IP Law LLP (57) ABSTRACT

An over-pressure control device prevents over-pressure conditions during the delivery of pressure treatment therapy to a patient with a respiratory treatment apparatus. The device may prevent delivered pressure from exceeding a first maximum pressure threshold. The device may also prevent the delivered pressure from exceeding a second maximum pressure threshold when the delivered pressure exceeds another pressure threshold for a period of time. In some embodiments, the second maximum pressure threshold may be lower than the first maximum pressure threshold. In an example embodiment, a set of comparators are configured to compare pressure with a maximum pressure threshold and to control a reduction in the pressure if the pressure exceeds the maximum pressure threshold. The set may also be config-
(Continued)

ured to compare the pressure with a pressure threshold and to control reduction in the maximum pressure threshold if the pressure exceeds the pressure threshold for a period of time.

24 Claims, 8 Drawing Sheets

(58) Field of Classification Search
CPC .......... A61M 16/0683; A61M 16/0666; A61M 16/0816; A61M 2205/42; A61M 16/0069; A61M 2205/18
USPC .......................... 128/204.18, 21, 22, 23, 24
See application file for complete search history.

(56) References Cited

U.S. PATENT DOCUMENTS

| | | | |
|---|---|---|---|
| 6,739,336 B1 * | 5/2004 | Jalde et al. | 128/204.21 |
| 6,840,240 B1 | 1/2005 | Berthon-Jones et al. | |
| 7,044,129 B1 | 5/2006 | Truschel et al. | |
| 7,267,122 B2 * | 9/2007 | Hill | 128/204.23 |
| 2004/0187870 A1 * | 9/2004 | Matthews et al. | 128/204.22 |
| 2006/0011195 A1 * | 1/2006 | Zarychta | A61M 16/00 128/200.14 |
| 2009/0272380 A1 * | 11/2009 | Jaffre et al. | 128/202.27 |
| 2013/0327331 A1 * | 12/2013 | Bourdon | 128/204.23 |

\* cited by examiner

PRESSURE CONTROL IN RESPIRATORY TREATMENT APPARATUS

CROSS-REFERENCE TO RELATED APPLICATIONS

This application claims the benefit of the filing dates of U.S. Provisional Patent Application Nos. 61/061,256 filed Jun. 13, 2008 and 61/097,591 filed Sep. 17, 2008, the disclosures of which are hereby incorporated herein by reference.

1. FIELD OF THE TECHNOLOGY

The present technology relates to methods and apparatus for controlling pressure. More specifically, it relates to methods and devices for controlling pressure in respiratory treatment apparatus such as continuous positive airway treatment devices, ventilator devices or other devices for treating conditions related to sleep disordered breathing.

2. BACKGROUND OF THE TECHNOLOGY

Respiratory treatment apparatus can function to supply a patient with a supply of clean breathable gas (usually air, with or without supplemental oxygen) at a therapeutic pressure or pressures, at appropriate times during the subject's breathing cycle. The therapeutic pressure is also known as the ventilation pressure.

Respiratory treatment apparatus typically include a flow generator, an air filter, a mask, an air delivery conduit connecting the flow generator to the mask, various sensors and a microprocessor-based controller. The flow generator may include a servo-controlled motor and an impeller. The flow generator may also include a valve capable of discharging air to atmosphere as a means for altering the pressure delivered to the patient as an alternative to motor speed control. The sensors measure, amongst other things, motor speed, gas volumetric flow rate and outlet pressure, such as with a pressure transducer or the like. The apparatus may optionally include a humidifier and/or heater elements in the path of the air delivery circuit. The controller may include data storage capacity with or without integrated data retrieval and display functions.

These devices may be used for the treatment of many conditions, for example respiratory insufficiency or failure due to lung, neuromuscular or musculoskeletal disease and diseases of respiratory control. They may also be used for conditions related to sleep disordered breathing (SDB) (including mild obstructive sleep apnea (OSA)), allergy induced upper airway obstruction or early viral infection of the upper airway.

Common to many forms of respiratory treatment apparatus is the need to control the pressure being applied to the patient. Some devices detect a peak pressure and compare it against a maximum threshold value. If the threshold value is exceeded an alarm state occurs, and corrective action may be taken. This corrective action can be a short-term reduction in supplied pressure, followed by an increase back to the previous pressure. Other devices have also been implemented to control pressure such as the system disclosed in U.S. Pat. No. 6,840,240 to Berthon-Jones et al.

It may be desirable to develop further methods and devices for controlling pressure in apparatus for treating upper respiratory conditions.

3. SUMMARY OF THE TECHNOLOGY

A first aspect of some embodiments of the technology is to provide methods and devices for checking pressure characteristics in apparatus that treat respiratory conditions.

A second aspect of some embodiments of the technology is to provide methods and devices for controlling pressure based on the checked pressure characteristics in apparatus that treat respiratory conditions.

Another aspect of some embodiments of the technology is to provide methods and devices for reducing pressure in apparatus based on checked pressure characteristics of a system that treats respiratory conditions.

In one aspect of the technology a pressure limit circuit is provided to detect and prevent the respiratory device from delivering a pressure above one or more pressure limits such as in the event of a system fault.

In another aspect of the technology one or more pressure limits is changed as a timed function of another limit.

In another aspect of the technology a pressure limit circuit to prevent an over pressure condition delivered by the respiratory treatment device is set at a first maximum pressure threshold. The first maximum pressure threshold is changed to a second maximum pressure threshold in response to the detection of a condition based on a third pressure threshold. Optionally, the first maximum pressure threshold is changed if a third pressure threshold is exceeded for a period of time. The first maximum pressure threshold may be greater than the second maximum pressure threshold. Additionally, the third pressure threshold may be approximately lower than or approximately equal to the second maximum pressure threshold. Optionally, the third pressure threshold may change if the third pressure threshold is exceeded for a period of time. Optionally, one or more of the pressure thresholds may stay at the changed limit(s) until a pressure delivered by the respiratory treatment apparatus falls below another pressure threshold. In this event, the pressure thresholds may return to their original settings.

In another aspect of the technology, at least two pressure limits govern the respiratory treatment apparatus to prevent an over-pressure condition. A first limit circuit is set to a first maximum pressure threshold and is configured to reduce pressure if the first maximum pressure threshold is reached or exceeded. In addition, a second limit circuit is set to a second maximum pressure threshold and is configured to reduce pressure as a condition of (a) the second maximum being reached or exceeded and (b) a third threshold has been exceeded for a period of time.

In some of the embodiments, the reduction in pressure may be implemented by triggering application of a brake of a flow generator motor.

In some of the embodiments, the reduction in pressure may be triggered within one or more breaths (e.g., one to five breaths) of an over limit condition. For example, a reduction of delivered pressure may be triggered within a few seconds (e.g., three seconds or less), if the first maximum pressure threshold is exceeded. Alternatively, the delivered pressure may be reduced below one of the pressure limit threshold, such as the second maximum pressure threshold, if the maximum pressure threshold is exceeded for about three breaths time (e.g., a time period of about three to seven seconds such as six seconds). In a certain preferred embodiment, the circuit may prevent the delivered pressure from going over a limit of 30 cmH2O for more than three breaths (e.g., six seconds at 30 breaths per second) in the event of a system failure or fault situation.

While the methodology may be implemented with software control and a microprocessor, in one embodiment the methodology may be implemented with comparator circuits and may optionally serve as a safety device for a respiratory treatment that delivers different pressure therapies with other therapy control components. In one embodiment of the circuit, a pressure limit comparator, which triggers a device for delivered pressure reduction, may be configured with multiple thresholds. The thresholds of this comparator may be dynamically changed based on detected pressure characteristics of the respiratory treatment apparatus or delivered pressure. For example, the pressure limit threshold of the pressure limit comparator may be changed with additional comparators, including, for example, a set of threshold-setting comparators. Essentially, the threshold-setting comparators dynamically set the pressure limit threshold of the pressure limit comparator. The set of threshold-setting comparators may implement (a) a timing period with a timing threshold and (2) a pressure trigger to initiate the timing period with a pressure threshold.

Optionally, in addition to braking or otherwise reducing pressure, an alarm may be generated based on the thresholds associated with the over-pressure conditions.

Additional features of the present respiratory technology will be apparent from a review of the following detailed discussion, drawings and claims.

A method for controlling pressure in a respiratory treatment device supplying pressurized gas to a patient, the method comprising the steps of:

preventing the pressure from being delivered above a first maximum pressure threshold;

determining the delivered gas pressure being supplied to the patient; and comparing the delivered gas pressure to a second lower pressure threshold, wherein if the delivered pressure equals or exceeds the second pressure threshold for more than a minimum period of time, the first pressure threshold is reduced until the delivered gas pressure is below a third pressure limit.

A pressure-limit control device to prevent an over-pressure condition of a respiratory treatment apparatus, the device comprising:

a first comparator set to compare a measure of pressure with a maximum pressure threshold and to control a reduction in the measure of pressure if the measure or pressure exceeds the maximum pressure threshold; and a second comparator set to compare the measure of pressure with a pressure threshold and to control reduction in the maximum pressure threshold if the measure of pressure exceeds the pressure threshold for a period of time.

An over-pressure detection device for a respiratory treatment apparatus comprising:

a first detection circuit configured to detect a first over-pressure condition comprising a measure of pressure exceeding a first pressure threshold;

a second detection circuit configured to detect a second over-pressure condition comprising a measure of pressure exceeding a second pressure threshold for a period of time represented by a timing threshold, the second pressure threshold being lower than the first pressure threshold; and a control circuit configured to control a motor driver for a flow generator of a respiratory treatment apparatus in response to a detection signal from either one of the first detection circuit and the second detection circuit.

The over-pressure detection device wherein the first over-pressure condition further comprises the measure of pressure exceeding the first pressure threshold for a period of time represented by a second timing threshold, the period of time represented by the second timing threshold being shorter than the period of time represented by the first timing threshold.

A pressure-limit control device to prevent an over-pressure condition of a respiratory treatment apparatus, the device comprising:

a first circuit to detect a signal representative of a measure of pressure exceeding a first threshold, the first threshold representative of a first pressure limit and to detect the exceeding of the first threshold by a second threshold, the second threshold representing a first time limit; and a second circuit to detect the signal representative of a measure of pressure exceeding a third threshold, the third threshold representative of a second pressure limit and to detect the exceeding of the third threshold by a fourth threshold, the fourth threshold representing a second time limit;

wherein the first and second pressure limits are different pressure limits and the first and second time limits are different time limits, and wherein a detection by either one of the first circuit and second circuit indicates an over-pressure condition of the respiratory treatment apparatus.

4. BRIEF DESCRIPTION OF DRAWINGS

The present technology is illustrated by way of example, and not by way of limitation, in the figures of the accompanying drawings, in which like reference numerals refer to similar elements including.

5. DETAILED DESCRIPTION

Figure 1:
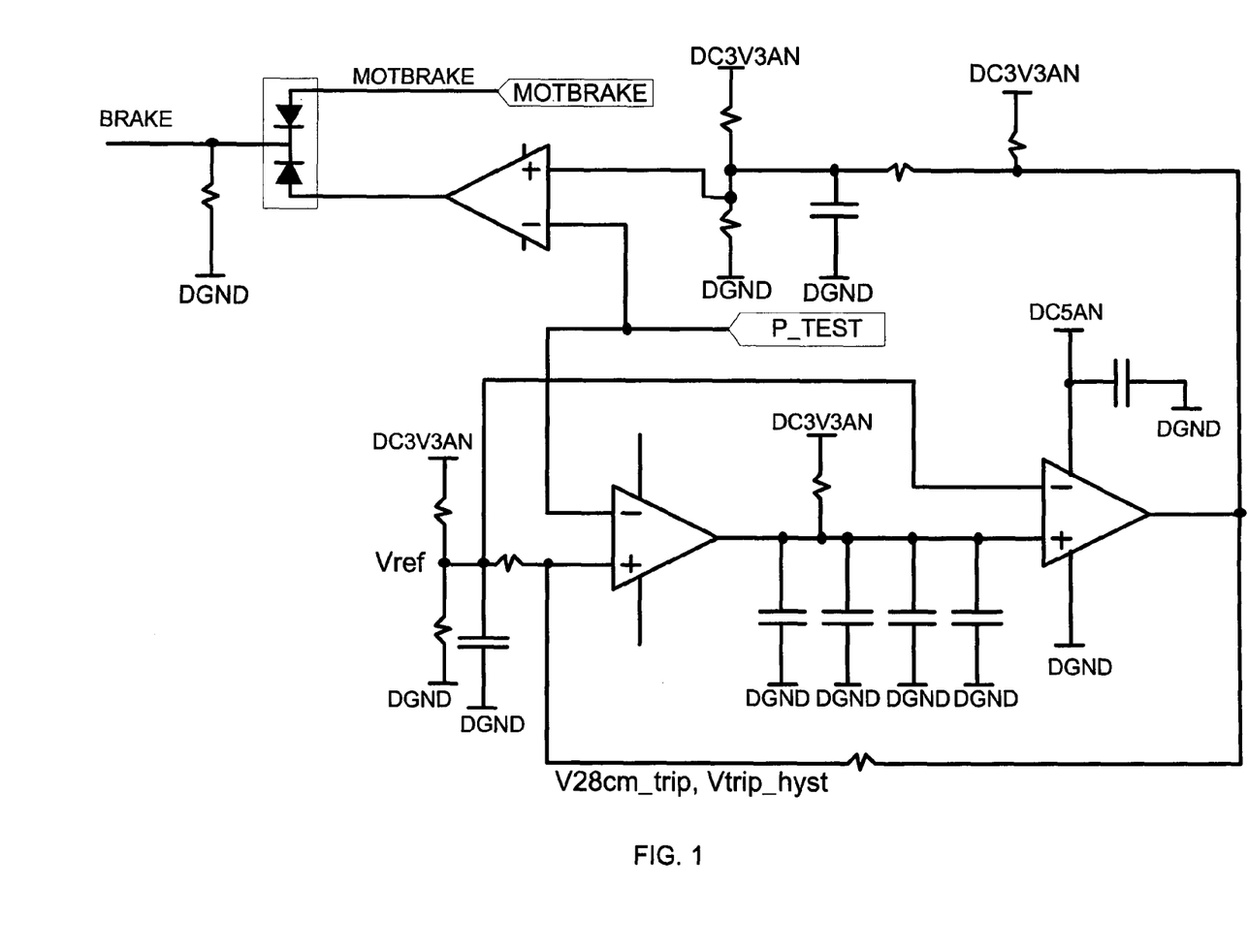
FIG. 1 shows an example circuit with comparators for controlling pressure of a respiratory treatment device to avoid an over-pressure situation such as that which may occur from a system fault.
Figure 2A:
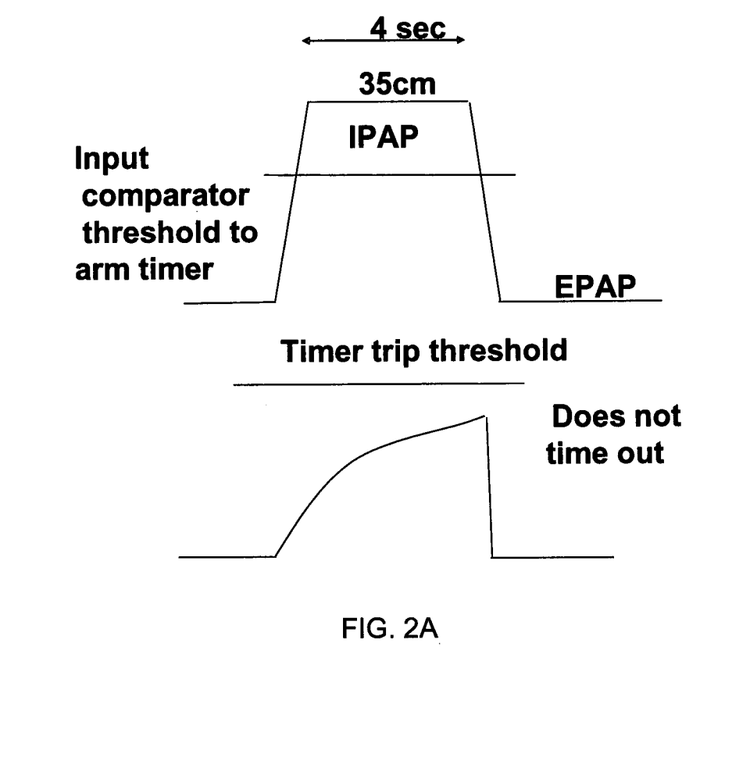
FIGS. 2A and 2B illustrates an operation of the embodiment of FIG. 1 without an overpressure condition and with an over-pressure condition respectively.
Figure 2B:
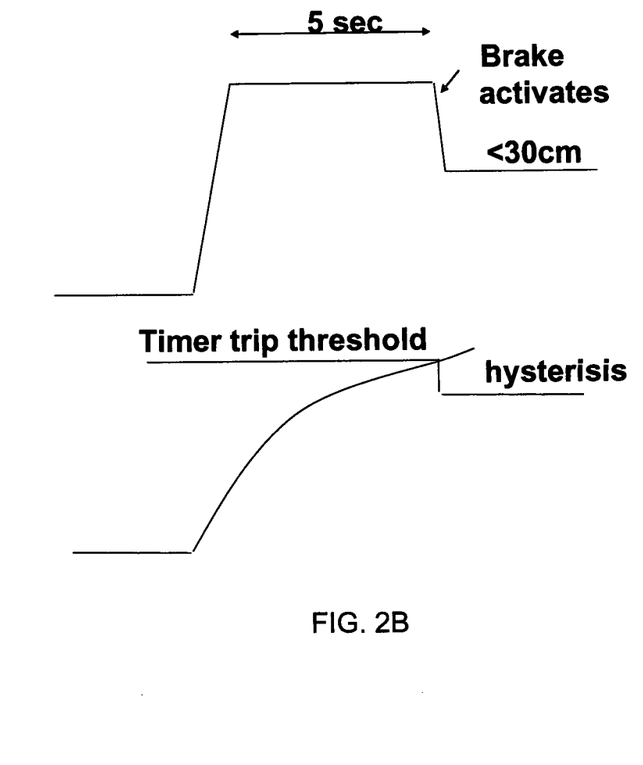

The embodiments of the present technology may be implemented with a drop over-pressure cut-out circuit such as the example circuit illustrated in FIG. 1. It will be understood that the circuit is merely an example embodiment and other components, hardware or software may be utilized to implement the methodologies described herein. The embodiment of the present technology may satisfy one or more standards such as to be compliant with regulatory requirements in a particular territory. For example, it may satisfy the following standards:

1. ISO 17510-1:2007: Sleep Apnoea Breathing Therapy—Part 1: Sleep Apnoea Breathing Therapy Equipment
2. ISO 10651-6:2004: Lung ventilators for medical use—Particular requirements for basic safety and essential performance—Part 6: Home care ventilatory support devices In such an example embodiment, the system may be configured to meet the following performance specifications:

1. The system may limit short-term mask pressure to less than 40 cmH2O within 1 second in any therapy mode when operating normally or in the presence of a single fault.
2. The system may limit the continuous mask pressure to less than 30 cmH2O within 6 seconds (or approximately three breaths delay) in any therapy mode when operating normally or in the presence of a single fault.

A. Example Design Methodology

The system may monitor the output pressure continually such as with a pressure sensor coupled with a mask or delivery tube from the respiratory treatment apparatus. Alternatively the pressure may be monitored at the output of the flow generator. Still further, the pressure may be determined using a pressure estimation algorithm based on flow and motor speed. Such a determination may be performed with software of a main therapy processor of the device or with an additional controller circuit or processor and software that may be distinct from the therapy control devices. With distinct pressure monitoring determination components, the pressure monitoring may be more immune to faults that could be caused within the therapy control components and software of the respiratory treatment device.

In the event that pressure is monitored remotely from a mask, adjustments to the measurements of pressure may be made to compensate for the remote location of the measurement, such as by compensating for delivery tube impedance, when the pressure limit is intended to be a limit of pressure at the mask. This may be accomplished by decreasing a pressure measurement made at a flow generator to compensate for a delivery tube impedance so that the measurement reflects a measurement of pressure at the mask. However, this remote determination may also be compensated for by making a suitable adjustment to the pressure limit thresholds discussed herein, such as by an increase in the chosen thresholds to compensate for any pressure drop that may be associated with a delivery tube or patient interface of the respiratory treatment apparatus. Such adjustments may be utilized to ensure accurate determination of pressure conditions at the mask so that mask over-pressure limits may be prevented at a desired standard with remote monitoring of pressure.

In normal operation of one embodiment, a pressure limit is set to a first limit such as an over-pressure threshold of 38 cmH2O, to satisfy a requirement for the pressure to be kept less than some max (e.g., 40 cmH2O).

If the output pressure exceeds a timer-related pressure threshold (e.g., 28.5 cmH2O) then a timer with a waiting period starts (e.g., a 5 second timer.) If at the end of the waiting period (e.g., 5 seconds) the delivered pressure is still above the timer-related pressure threshold (e.g., 28.5 cm) then the first limit or over-pressure threshold is lowered to a second limit using a second over-pressure threshold, that may be about the quantity of the timer-related pressure threshold (e.g., 28 cmH2O) thereby meeting a requirement that the delivered pressure is less than a desired max limit (e.g., 30 cmH2O) in single fault conditions. The timer-related pressure threshold may then be lowered (e.g., to 25 cmH2O) to provide some hysterisis to prevent the timer from being reset if the delivered pressure momentarily drops below the former threshold 28 cm due to overshoot in a pressure reduction process such as by braking a blower motor of a flow generator. The over-pressure limit then remains at the changed level (e.g., a second over-pressure threshold of 28 cm) so long as the delivered pressure continues to exceed the timer-related pressure threshold (e.g., 25 cmH2O). Once the delivered pressure drops below this timer-related pressure threshold (e.g., 25 cmH2O), the timer is reset. Optionally, the over-pressure threshold and the timer-related pressure threshold may be returned to the original settings.

In normal operation mode of some embodiments, a maximum time the pressure would need to exceed 28.5 cm is the maximum IPAP (inspiratory positive airway pressure) duration of about 4 seconds.

During a treatment mode of some embodiments, such as a CPAP mode, it is expected that a threshold of about 28.5 cmH2O would not be exceeded.

An example embodiment of the technology may be a circuit that includes the following components:

An input 28 cmH2O comparator with hysterisis
The input comparator may arm or trigger a timer circuit with a timing period (e.g., five seconds)
A timer comparator
The time comparator may be five seconds. Typically, it will be longer than a max inspiratory positive airway pressure time (e.g., 4 seconds) but less than approximately three breaths (e.g., 6 seconds).
A switchable pressure limit comparator
This may be configured to trigger a device for pressure reduction, such as a blower motor brake of a flow generator. This may be set to a first pressure limit threshold (e.g., 40 cmH2O) if the above-mentioned timer has not expired. The threshold may be changed to a second pressure limit threshold if the timer has expired.

B. Comparator Threshold Design Equations

The following equations may be utilized to determine (a) the comparator trip voltage reference when the output of the timer is low and (b) the pressure associated with the voltage. In the following example calculations, values for the resistors are given and an example 28 cmH2O threshold is used:

$$Vref = \frac{R_{110}}{R_{110} + R_{111}} \times 3.3\,V = \frac{1k}{1k + 1.5k} \times 3.3 = 1.32\,V$$

$$V28cm\_trip \cong Vref \times \frac{R_{109}}{R_{109} + R_{108}}$$

$$= 1.32 \times \frac{1Meg}{1Meg + 39k}$$

$$= 1.27\,V$$

$$P28cm\_trip = \frac{(V28cm\_trip - 2.95)}{-0.0611} = 27.5\,cmH2O$$

The above Ptrip equation may also optionally take into account the voltages associated with an analog to digital conversion of a pressure signal from an analog pressure sensor.

With some pressure sensing systems, there can be noise within the signal from the sensor. This noise may tend to reset the timer. Thus, there may be a band of operation in which the noise could reset a timer and effectively shift the reliable trip point or pressure limit threshold to a higher pressure. For example, a band of uncertainty could be around 0.8 cm.

Thus, in one embodiment, in order to avoid the impact of such resets from the pressure channel noise, a trip point or timer-related pressure threshold may be implemented at about 28 cm. Optionally or additionally, filtering may be implemented to reduce the impact of pressure channel noise. For example, a low pass filter, such as an analog filter, on a pressure signal of a pressure sensor may filter out some level of noise such as the 0.8 cm of pressure noise mentioned. This could be accomplished with a fairly long time constant, such as about 100 ms, to filter narrow pressure spikes which can reset the 5 sec timer.

Once the timer trips due to the timer-related pressure threshold, the hysteresis resistor increases the trip voltage of the circuit and hence reduces the trip pressure or timer-related pressure threshold. This may be given by the following equations in the example embodiment using Vhi=2.603V calculated below in the output pressure limiter comparator section.

$$\text{Vtrip\_hyst} = \textit{Vref} + \frac{R_{109}}{R_{109} + R_{108}} \times (\textit{Vhi} - \textit{Vref})$$

$$= 1.32 + \frac{39k}{39k + 1 Meg} \times (2.603 - 1.32)$$

$$= 1.368$$

$$\text{Ptrip\_hyst} = \frac{1.368 - 2.95}{-0.0611} = 25.9 \, cmH2O$$

Hence, an example reset point may then be implemented at around 26.5 cm.

This example is well below the overpressure comparator minimum trip point and provides a margin against the pressure momentarily dropping below the hysterisis trip pressure.

C. Timer Time Constant Design Equations

In some embodiments, a timeout of 5 seconds may be implemented to allow the delivered pressure to stay at less than (<) a certain threshold (e.g., 37 cmH2O) for a period of time (e.g., for up to 6 seconds) before the over-pressure threshold limit is reduced, for example, to a second over-pressure limit such as 28 cmH2O, to then limit the delivered pressure to less than another desired maximum pressure value (e.g., a standard that requires 30 cm.)

In the following example calculations, the comparator reference Vref is the same voltage as used in the input 25 cm comparator (e.g., 1.32V).

The following equation derives the implemented time constant to achieve a 5 second mono-stable period.

$$\tau = \frac{5 sec}{\ln\left(\frac{Vfinal}{Vfinal - Vref}\right)}$$

$$= \frac{5 sec}{\ln\left(\frac{3.3}{3.3 - 1.32}\right)}$$

$$= 9.79 sec$$

If we set the timing capacitor to 4×1 uF, we select a 2.4MΩ timing resistor.

$$\text{time} = \tau \ln\left(\frac{Vfinal}{Vfinal - Vref}\right)$$

$$= 4uF \times 2M4 \times \ln\left(\frac{3.3}{3.3 - 1.32}\right)$$

$$= 4.9 sec$$

A dual comparator, such as a comparator model # LMC6772B from National Semiconductor, may be used. However, other comparators may also be implemented. The LMC6772B has open collector outputs with low output and input leakage currents specified. The input leakage current is typically <0.1 pA at 25° C. The output leakage current is 0.1 nA typical at $V_{out}$=15V and 500 nA worse case at $V_{out}$=15V and 25° C. Hence, the leakage current is dominated by the output leakage. The output leakage will typically flow into the output pin thereby increasing the duration of the timeout.

Because the input common range goes down to ground for the LMC6772B, the trip thresholds will be well within the common mode range of the device.

Figure 3:
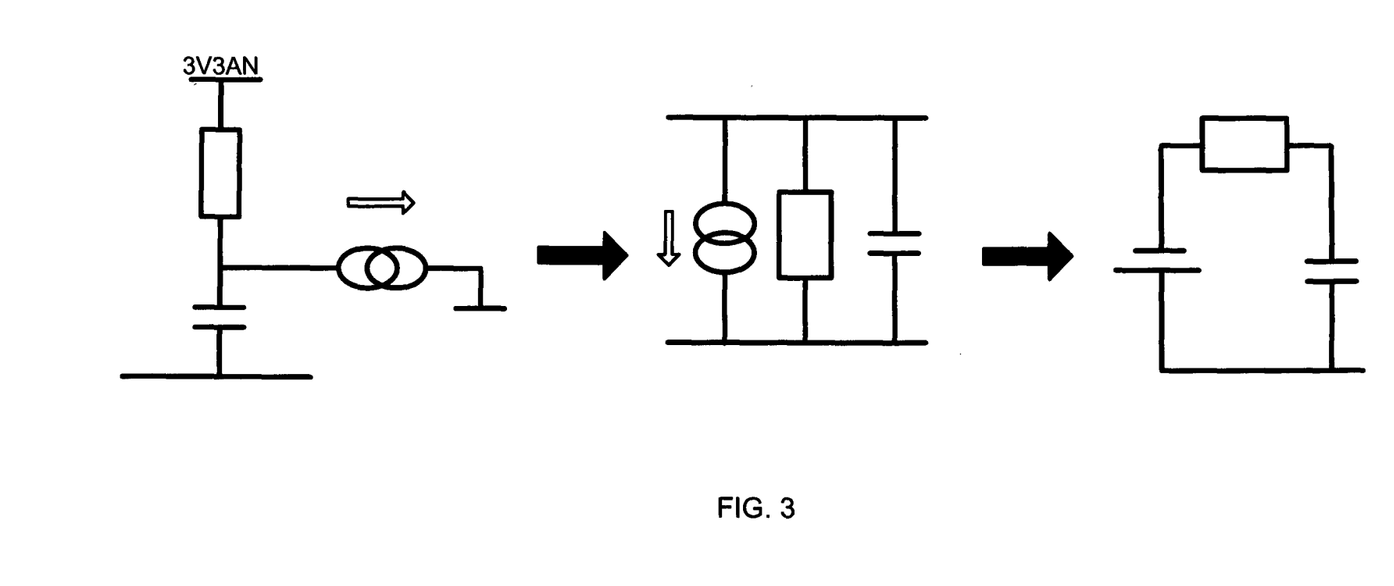
FIG. 3 illustrates a method of determining an Thevenin equivalent.

D. Effect of Leakage Current Upon Timer Accuracy:

The leakage current at the reference input has no effect due to the low impedance of the reference circuit. The leakage current on the other input is integrated up by the timer capacitor during the timer charging period and acts as an offset to the comparator trip point. This is shown in the following equivalent circuit from the theory of superposition. In such a determination, the contributions by the leakage current voltage sources are short circuited out of the circuit. We then apply the Thevenin equivalent circuit to derive the equivalent circuit. Note that the leakage current always flows into the output pin due to the open collector output. An example of the Thevenin equivalent analysis is illustrated in FIG. 3.

The effect of the bias current is given by the following equation given a 4.9 sec timer period and a 10.44 sec time constant:

$$V\text{offset} = I\text{leak} \times R\text{timer} \times (1 - e^{-t/R\text{timer}C\text{timer}}) = I\text{leak} \times R\text{timer} \times (1 - e^{-4.9/9.6}) = I\text{leak} \times R\text{timer} \times 0.4$$

The output leakage current of the LMC6772 is typically 0.1 nA at 25° C. at 15V output, but worse case is 500 nA. In practice the timer of the embodiment operates from 0 to 1.32V hence the leakage will be an order of magnitude lower based on the datasheet plot of leakage current versus output voltage. Hence, 50 nA is a reasonable worse case at 25° C. The circuit is directly above the inlet hence will run cool, so if we assume a worse case temperature of 35° C., we could double the leakage current due to the higher temperature. Hence 100 nA is a reasonable worse case over the operating temperature range.

This gives a 100 mV worse case offset over the flow generator operating temperature range. This corresponds to a 500 ms (i.e., 10%) error in the 4.9 sec timeout case. Note that since the leakage current only flows into the pin due to the open collector output, the leakage current can only increase the time constant.

This is not significant when compared with the 4 second maximum IPAP period and the system implementation for the timeout to be less than (<) 6 seconds. This gives a timer tolerance as ±1 sec (i.e., ±20%).

Some example component tolerances for the present embodiment are as follows:

| Parameter | Tolerance |
| --- | --- |
| Timer resistor tolerance | ±1% |
| Timer capacitor tolerance | ±10% |
| X7R Timer Capacitor temperature coefficient over 0 to 50° C. range | −10% (+/−15% spec but from 0 to 50° C. most caps are <−5%) caps are mounted in cool position above air inlet to limit temperature rise. |
| Offset (due to 100 nA Leakage current and 5 mV comparator offset) | +0 mV to +100 mV(= 0.5 sec = +10%[1]) |
| Total | −21% to +22% (i.e. 3.9 to 5.98 secs) |

[1]Note that leakage flowing into comparator output pin can only increase time period.

Note that as the temperature increases, the leakage increases, which will increase the trip time. However this will be somewhat offset by the negative temperature coefficient (tempco) of the X7R capacitor material which will tend to reduce the trip time. Leakage can only increase the timer period while the tempco of the capacitor can only reduce the timer period.

Hence, the designed embodiment would meet the 6 second upper limit but is just under the 4 second lower limit even in a worse case condition. In practice, the tolerances are unlikely to raise to the worse case. Even if the timer timed out with a 4 second IPAP high pressure period the effect would only be to reduce the IPAP pressure for 100 ms at the end of IPAP. Under most use scenarios, the delivered pressure will be below the over pressure trip point at the end of the 4 second IPAP so there should be no observable effect due to leakage current.

E. Output Comparator Thresholds Design Equations

In the embodiment of FIG. 1, the output comparator has two thresholds (e.g., 28 and 37 cmH2O) that are applied depending on the status of the timer (e.g., the 5 sec mono-stable). The mono-stable is an open collector output, hence, the output is either close to ground for the first threshold (e.g., 37 cmH2O limit) or floats to the value set by the resistor network at the output to achieve the second threshold (e.g., 28 cmH2O limit). This gives the following two resistor topologies as defined by the mono-stable output.

Figure 4:
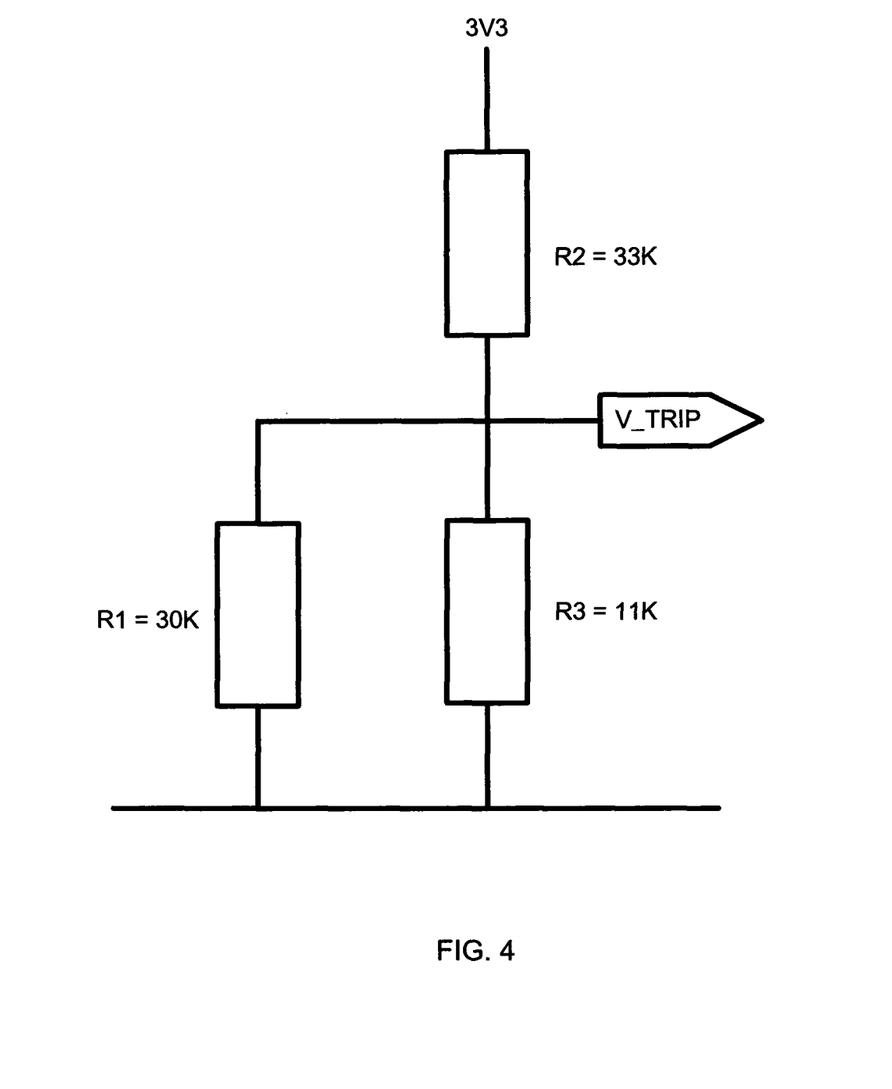
FIG. 4 illustrates a Thevenin equivalent for the embodiment of FIG. 1 in a state with the first pressure limit threshold applied to the pressure limit comparator.

F. Mono-Stable Output Low (37 cmH2O Pressure Limit Applied):

FIG. 4 shows an equivalent circuit for the resistor network in this state where the first pressure limit is applied to the comparator. There may be a small error due to the output of the comparator sitting a VCEsat above ground instead of at ground. However, the effect of this is small and will tend to reduce the trip pressure slightly below the first threshold (e.g., 37 cmH2O), which is in the safe direction.

The following design equations may be used to calculate the trip pressure or the over-pressure threshold from the given resistor values.

$$Vtrip = \frac{R1 \| R3}{R1 \| R3 + R2} \times 3.3V = \frac{\frac{R1 \times R3}{R1 + R3}}{\frac{R1 \times R3}{R1 + R3} + R2} \times 3.3 = 0.6471 \, V$$

$$Ptrip = \frac{(Vtrip - 2.95)}{-0.0611} = 37.6 \, cmH2O$$

Applying a ±5% tolerance to this to allow for sensor channel errors gives a threshold range of 35.7 to 39.5 cmH2O. Hence, the output comparator threshold would be less than the 40 cmH2O limit in the standard noted above.

In practice the output of the comparator will not reach ground, but rather it will reach the output saturation voltage of typically 250 mV (400 mV worse case). This will shift the Vtrip voltage up a small amount and hence reduce the pressure slightly as shown in the following equations. From superposition the shifts in output due to 400 mV and 250 mV of saturation voltage are given by:

$$Vtrip\_shif\_worse\_case = 400 \, mV \times \frac{33K \| 11K}{33K \| 11K + 30K} = 86.3 \, mV$$

$$Vtrip\_shift\_typical = 250 \, mV \times \frac{33K \| 11K}{33K \| 11K + 30K} = 53.9 \, mV$$

$$Ptrip\_typical = \frac{0.6471 + 0.0539 - 2.95}{-0.0611} = 36.8 \, cmH2O$$

Hence the nominal over pressure threshold will be around 36.8 cm H2O depending on the comparator output saturation voltage.

Figure 5:
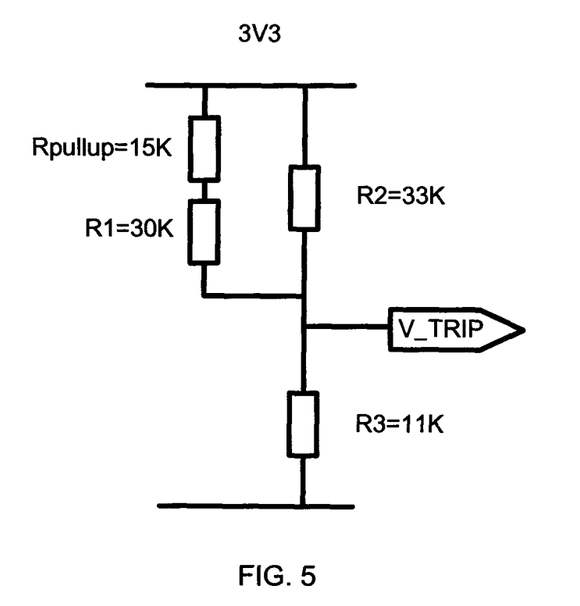
FIG. 5 illustrates a Thevenin equivalent for the embodiment of FIG. 1 in a state with a second pressure limit threshold applied to the pressure limit comparator.

G. Mono-Stable Output Off (28 cmH2O Pressure Limit Applied):

FIG. 5 illustrates an equivalent circuit for the resistor network in the state where the second pressure limit threshold (e.g., 28 cmH2O) is applied to the comparator.

The following design equations may be used to calculate the trip pressure from the given resistor values.

$$Vtrip = \frac{R3}{(R1 + Rpullup) \| R2 + R3} \times 3.3 \, V$$

$$= \frac{11K}{\frac{(15K + 30K) \times 33K}{15K + 30K + 3K} + 11K} \times 3.3$$

$$= 1.2085 \, V$$

$$Ptrip = \frac{(Vtrip - 2.95)}{-0.0611}$$

$$= \frac{(1.2085 - 2.95)}{-0.0611}$$

$$= 28.5 \, cmH2O$$

Applying a ±5% tolerance to this calculation to allow for sensor channel errors gives a threshold range of 27.1 to 29.9 cmH2O. Hence, the example output comparator threshold is guaranteed to be less than the 30 cmH2O limit in the CPAP standard noted above.

When the timer comparator output is high the comparator output voltage (Vhi) is given by the following equations. This voltage is used to drive the hysteresis in the input comparator. In other words, when the timer comparator output steps up from zero volts to this voltage it provides the drive to a hysteresis.

$$Vhi = 3.3 - \frac{Rpullup}{Rpullup + R1} \times (3.3 - Vtrip\_hi)$$

$$= 3.3 - \frac{15k}{15k + 30K} \times (3.3 - 1.2085)$$

$$= 2.603 \, V$$

H. Further Example Design Methodology

Figure 6:
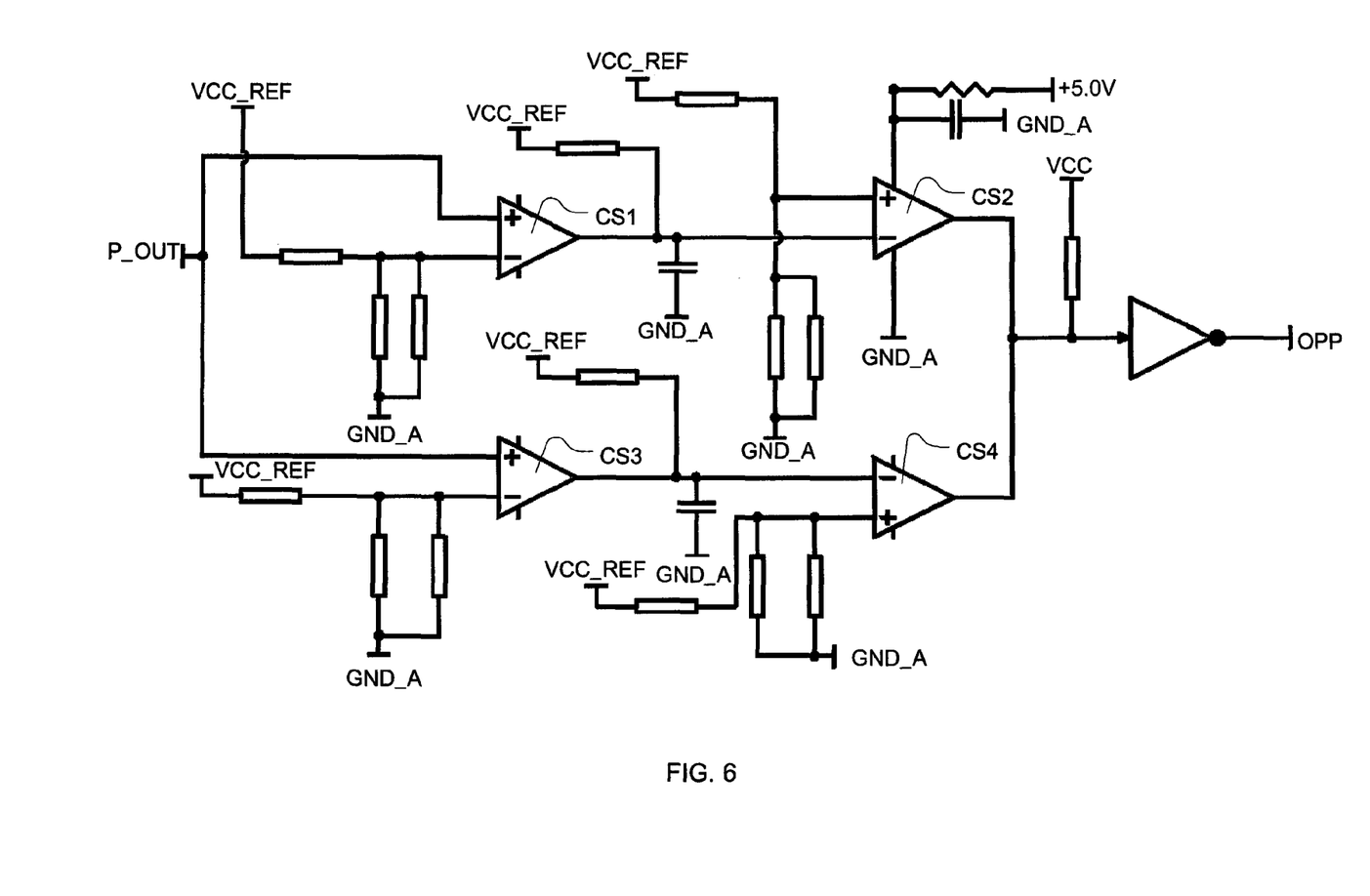
FIG. 6 is a circuit schematic illustrating a further example embodiment of an over-pressure detection circuit.

FIG. 6 illustrates a further embodiment of an over-pressure cutoff circuit of the present technology. The circuit employs two sets of comparators, which may optionally have a common or complementary component design. For example, as illustrated in FIG. 6, each comparator set detects whether a different pressure limit has been exceeded for a different period of time. For example, a first comparator set CS1, CS2 implements a detection of a condition associated with a measure of pressure (e.g., an output signal of a pressure sensor—shown as signal "P_Out" in FIG. 6). A first comparator CS1 or pressure comparator detects whether the measure of pressure exceeds a first threshold representative of a first pressure limit. Based on an output of the first comparator CS2 and a second threshold, a second comparator CS2 or timing comparator detects whether the first pressure limit is exceeded for a period of time. Thus, the second threshold may represent a first time limit.

Similarly, a second comparator set CS3, CS4 implements a detection of a condition associated with the same measure of pressure P_OUT. A third comparator CS3 or pressure comparator detects whether the measure of pressure exceeds a third threshold representative of a second pressure limit. Based on an output of the third comparator CS2 and a fourth threshold, a fourth comparator CS4 or timing comparator detects whether the second pressure limit is exceeded for a period of time. Thus, the second threshold may represent a second time limit.

By adjusting the circuit elements, for example by selecting certain circuit elements based on their specifications (e.g., capacitance of capacitors, resistance of resistors, etc.), the circuit may be configured to implement different pressure condition detections. For example, the first circuit set including a pressure detection capacitor and timer capacitor (e.g., CS1 and CS2 respectively) may implement a detection of a pressure at or near 40 cm $H_2O$ (e.g., above an approximately 38 cm $H_2O$ threshold) for a short period of time less than 1 second (e.g., a split second or fractional second threshold). Similarly, the second set including a pressure detection capacitor and timer capacitor (CS3 and CS4 respectively) may implement a detection of a pressure at or near 30 cm $H_2O$ (e.g., above an approximately 28 cm $H_2O$ threshold) for a period of time that exceeds several seconds (e.g., about a 5 second threshold).

Either output of the first and second comparator sets may then serve as an over-pressure trigger or detection signal (shown in FIG. 6 as signal "OPP"). For example, the detection signal may be supplied to a motor controller as a braking signal like the embodiment previously discussed. However, the signal may also be supplied to a motor controller as a termination signal. Thus, the signal based on both comparator sets may serve as a shut down signal for a flow generator or a reduce speed signal for a flow generator speed.

I. Example System Implementation

Figure 7:
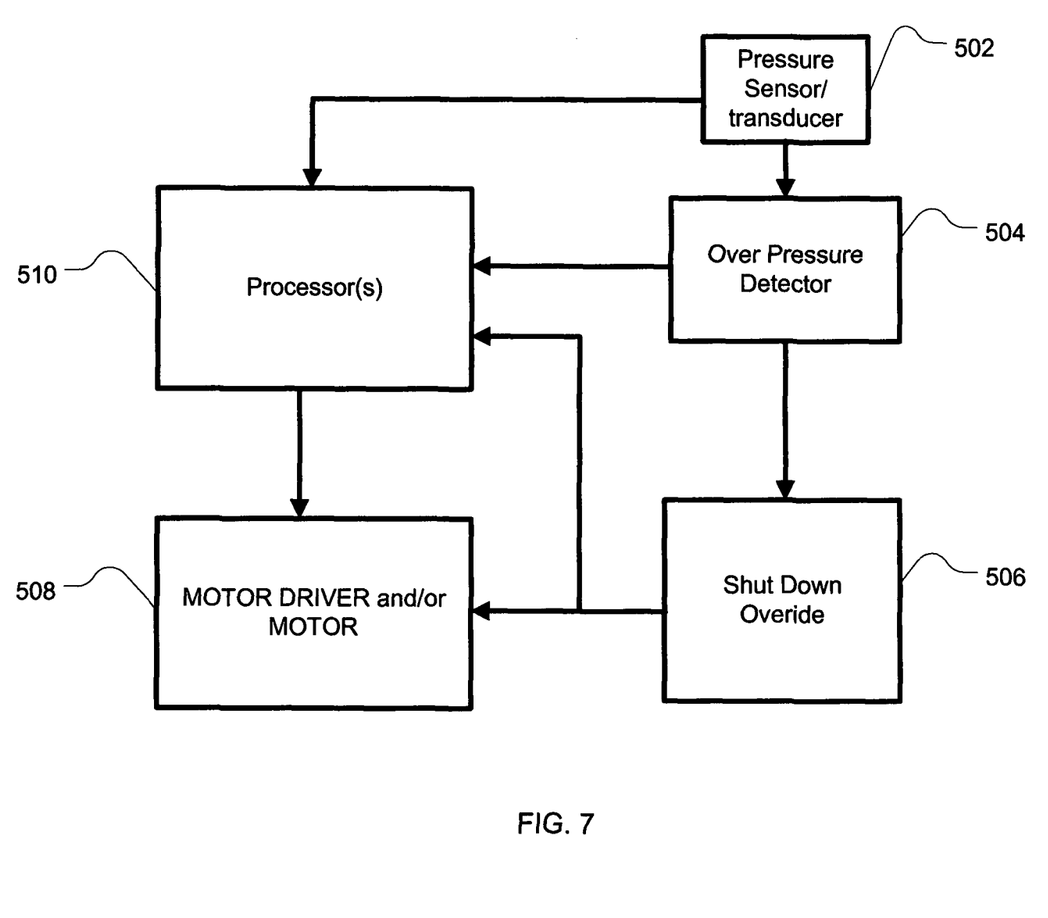
FIG. 7 is a system diagram illustrating an example implementation of an over-pressure detector with some components of a respiratory treatment apparatus.

For example, a system for implementing a shut down or flow generator override is illustrated in FIG. 7. Typical components for such a system may include one or more processors 510 or a programmable processor with memory (not shown), a pressure sensor or transducer 502, an over-pressure detector 504 of any of the embodiments previously discussed, an optional shut down override circuit 506 and a motor driver and/or motor 508 of a flow generator. In such as system, the processor may implement a software-based control of the motor of the flow generator. The software may be configured with software algorithms to set a treatment pressure. It may also include algorithms to enforce multiple and distinct limits based on pressure and time such as, for example, those previously discussed with respect to ISO 17510-1:2007 and/or ISO 10651-6:2004. For example, a pressure setting algorithm of a memory may control the processor to calculate a pressure setting to be delivered by the blower. The setting may be reduced by the processor if the processor detects that the setting would exceed the programmed limits (e.g., if the measure of pressure exceeds a limit (e.g., 38 cm $H_2O$) for a fraction of a second and/or if the measure of pressure exceeds another limit (e.g., 28 cm $H_2O$) for more than a period of time (e.g., five seconds)) determined by the processor in conjunction with a measure of pressure from the pressure sensor 502. Optionally, if either condition is detected by the processor, the processor may simply shut down the motor of the flow generator.

Figure 8:
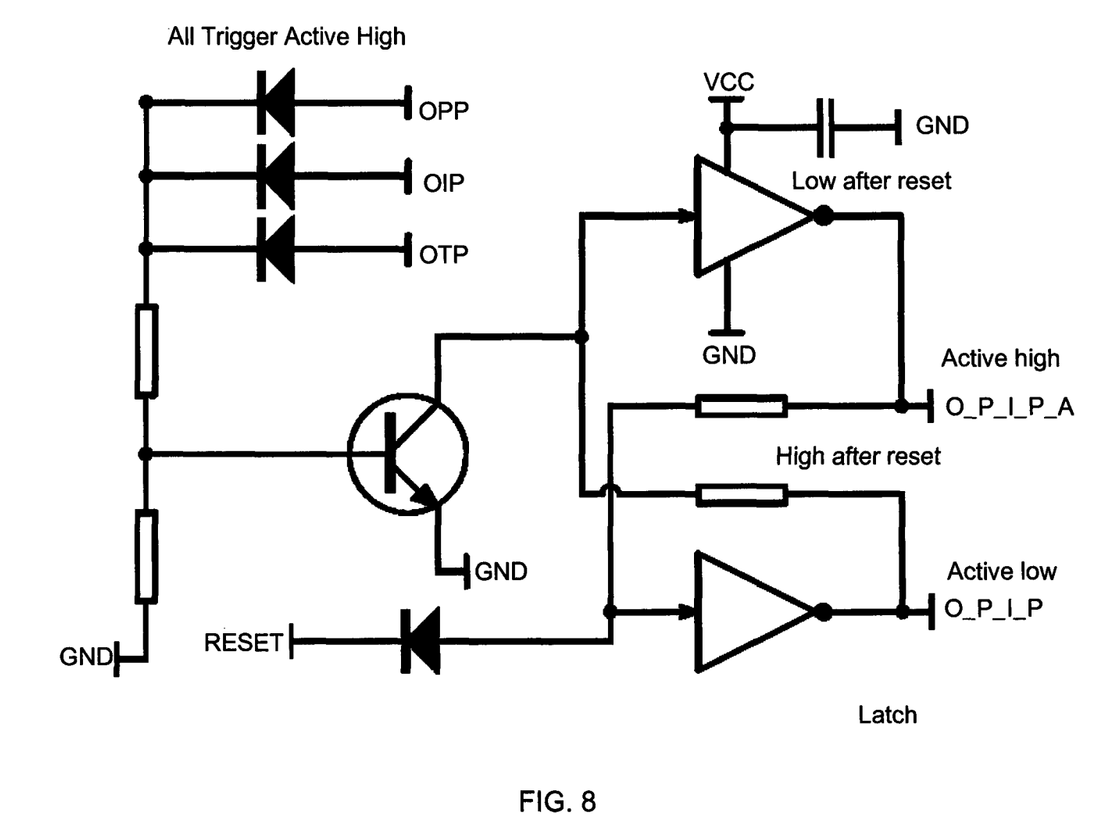
FIG. 8 is a circuit schematic with components for an example shut down circuit suitable for use in the system of FIG. 7.

However, the over-pressure detector 504 may also serve as an additional protection circuit to enforce similar limits or the same limits as the processing circuit. Thus, in the event of a software or processor fault, the over-pressure detector 504 may still brake or stop the motor of the flow generator. Thus, a brake or stop signal may be provided to the motor or motor driver based on a signal from the over-pressure detector that is independent from the pressure setting control algorithms of the processor. For example, the over-pressure detector may set a shut down override circuit for the motor. The shut down override circuit would then deactivate the motor. For example, as illustrated in FIG. 8, the shut down override circuit may include a memory or latch circuit that in turn can control a switch, such as a transistor, of the motor driver. The switch may be configured to de-power the motor based on the state of the override circuit. In the embodiment, an over-pressure detection signal (shown as OPP) may set the override latch based on the detection of the over-pressure detector, such as by changing its state to a shut down state. In the embodiment, that shut down state would then in turn control the motor to prevent electrical current to drive the motor.

In other embodiments, the detection signal of the over-pressure detector may more directly control an operation termination switch of the motor driver of the flow generator without the illustrated shut down override circuit of FIG. 8. However, the illustrated embodiment of the override circuit may be particularly useful in the event multiple sensors are utilized for shutting down the motor. For example, an optional over current detector (not shown) may also supply a detection signal such as an over-current detection signal (shown as OIP) to change the state of the override circuit. Similarly, an optional over temperature detector (not shown) may also supply a detection signal such as an over-temperature detection signal (shown as OTP) to change the state of the override circuit. In such embodiments, any of the detection signals may trigger the shut down of the motor.

Optionally, the over-pressure detector and/or shut down override 506 may provide status signals to the processor. Thus, an over-pressure detection signal from the over-pressure detector may indicate to the processor that an over-pressure condition has been detected. Alternatively, the over-pressure detection signal may provide such a signal to the processor and/or an output device such as an LED that indicates which of the over-protection conditions have been detected. Thus, with the signals from the over pressure detector, the processor may be informed of the detection situation and record the information in memory of the device. The processor may then shut down or terminate processing or pressure treatment processing in response to the detection situation determined by the over-pressure detector 504. The processor may also in turn record in a memory the state of the processing (e.g., registers and variables of the programming or pressure setting algorithms) and the state of the system (e.g., pressure settings, pressure measurements, present time etc.) in response to the signals of either of the shut down circuit or over-pressure sensor to permit later debugging of the problem with the apparatus or processor.

In the foregoing description and in the accompanying drawings, specific terminology, equations and drawing symbols are set forth to provide a thorough understanding of the present technology. In some instances, the terminology and symbols may imply specific details that are not required to practice the technology. Moreover, although the technology herein has been described with reference to particular embodiments, it is to be understood that these embodiments are merely illustrative of the principles and applications of the technology. It is therefore to be understood that numerous modifications may be made to the illustrative embodiments and that other arrangements may be devised without departing from the spirit and scope of the technology. For example, the comparisons implemented by the comparators may be implemented by software in a digital microprocessor. The software may be stored in a memory of the device and/or be supplied by a suitable digital storage medium.

The invention claimed is:

1. A method for controlling pressure in a respiratory treatment device supplying pressurized gas to a patient, the method comprising:
   preventing the pressure from being delivered above a first maximum pressure threshold;
   determining a delivered gas pressure being supplied to the patient with a sensor; and
   in a control circuit of the respiratory treatment device, comparing the delivered gas pressure to a second pressure threshold, the second pressure threshold lower than the first maximum pressure threshold, wherein if the delivered gas pressure equals or exceeds the second pressure threshold for more than a minimum period of time, the first maximum pressure threshold is reduced until the delivered gas pressure is below a third pressure threshold.

2. In a respiratory treatment apparatus, a pressure limit control method to prevent an over-pressure condition delivered by the respiratory treatment apparatus comprising:
   setting a pressure limit device to a first maximum pressure threshold; and
   setting the pressure limit device to change from the first maximum pressure threshold to a second maximum pressure threshold in response to a detection of a condition based on a third pressure threshold,
   wherein each maximum pressure threshold is applied to permit delivered pressure below its maximum with the pressure limit device,
   whereby an over-pressure condition delivered by a respiratory treatment apparatus may be prevented.

3. The control method of claim 2 wherein the detection of the condition comprises determining that a measure of pressure exceeds the third pressure threshold for a period of time.

4. The control method of claim 2 wherein the first maximum pressure threshold is greater than the second maximum pressure threshold.

5. The control method of claim 4 wherein the third pressure threshold is lower than the second maximum pressure threshold.

6. The control method of claim 5 wherein the third pressure threshold is adjusted if the third pressure threshold is exceeded for a period of time.

7. A pressure-limit control device to prevent an over-pressure condition of a respiratory treatment apparatus, the device comprising:
   a first comparator set to compare a measure of pressure with a maximum pressure threshold and to control a reduction in the measure of pressure if the measure of pressure exceeds the maximum pressure threshold; and
   a second comparator set to compare the measure of pressure with a second pressure threshold and to control reduction in the maximum pressure threshold if the measure of pressure exceeds the second pressure threshold for a period of time, wherein the maximum pressure threshold is reduced until the measure of pressure is equal to or below a third pressure threshold.

8. The device of claim 7 wherein the first comparator set controls a brake for a motor of a flow generator.

9. The device of claim 7 wherein the period of time comprises 4 seconds.

10. A pressure-limit control device of claim 7 further comprising a respiratory treatment apparatus, wherein the respiratory treatment apparatus comprises:
    a flow generator configured to produce a breathable gas for a patient at a pressure above atmospheric pressure;
    a controller configured to control the flow generator to produce the breathable gas according to a pressure therapy regime; and
    a pressure sensor to determine a measure of pressure associated with the pressure delivered by the flow generator.

11. An over-pressure detection device for a respiratory treatment apparatus comprising:
    a first detection circuit configured to detect a first over-pressure condition comprising a measure of pressure exceeding a first pressure threshold;
    a second detection circuit configured to detect a second over-pressure condition comprising a measure of pressure exceeding a second pressure threshold for a period of time represented by a first timing threshold, the second pressure threshold being lower than the first pressure threshold; and
    a control circuit configured to control a motor driver for a flow generator of a respiratory treatment apparatus in response to a detection signal from either one of the first detection circuit and the second detection circuit.

12. The over-pressure detection device of claim 11 wherein the first over-pressure condition of the first detection circuit further comprises the measure of pressure exceeding the first pressure threshold for a period of time represented by a second timing threshold, the period of time represented by the second timing threshold being shorter than the period of time represented by the first timing threshold.

13. The over-pressure detection device of claim 11 wherein the control circuit is configured to activate a brake for a motor of the flow generator.

14. The over-pressure detection device of claim 11 wherein the control circuit is configured to de-activate a motor of the flow generator.

15. The device of claim 11, wherein the first pressure threshold is representative of a first pressure limit and wherein the device detects the exceeding of the first pressure threshold by a first time threshold, the first time threshold representing a first time limit; and
    wherein the second pressure threshold is representative of a second pressure limit and the device detects the exceeding of the second pressure threshold by a second time threshold, the second time threshold representing a second time limit; wherein the first and second pressure limits are different pressure limits and the first and second time limits are different time limits, and wherein a detection by either one of the first detection circuit and second detection circuit indicates an over-pressure condition of the respiratory treatment apparatus.

16. The device of claim 15 further comprising a pressure sensor to generate a signal representative of the measure of pressure.

17. The device of claim 16 wherein the motor driver is coupled with the first detection circuit and second detection circuit and, wherein the motor driver is configured to shut down a motor based an output of the first detection circuit and second detection circuit.

18. The device of claim 17 further comprising a blower motor coupled to the motor driver.

19. The device of claim 17 further comprising a processor coupled to first circuit and second circuit, the processor configured to receive a detection signal from the first and second circuits, wherein the motor driver is configured to shut down a motor controlled by the processor independently of motor control processing of the processor.

20. The device of claim 15 further comprising a respiratory treatment apparatus, wherein the respiratory treatment apparatus comprises:
a flow generator coupled with the over-pressure detection device wherein the over-pressure detection device is configured to limit operation of the flow generator based on a detection signal of the over-pressure detection device.

21. The device of claim 20 further comprising a pressure sensor coupled with the over-pressure detection device, the pressure sensor to generate a signal representative of a measure of pressure to the over-pressure detection device.

22. The device of claim 21 wherein the flow generator comprises a motor driver and wherein the motor driver is configured to shut down the flow generator based on an output signal of the over-pressure detection device.

23. The device of claim 22 further comprising a processor coupled with the flow generator to control the flow generator and the over-pressure detection device, the processor configured to receive a detection signal from over-pressure detection device, wherein the motor driver is configured to shut down the flow generator controlled by the processor independently of flow generator control processing of the processor.

24. The device of claim 15, wherein the first detection circuit comprises a first comparator set configured to detect the first pressure limit based on the first time limit and the second detection circuit comprises a second comparator set configured to detect the second pressure limit based on the second time limit.

* * * * *